(12) United States Patent
Abbasi

(10) Patent No.: US 9,313,977 B2
(45) Date of Patent: Apr. 19, 2016

(54) ABBASI STRAIN OF RICE

(71) Applicant: Fida M. Abbasi, Mansehra (PK)

(72) Inventor: Fida M. Abbasi, Mansehra (PK)

( * ) Notice: Subject to any disclaimer, the term of this patent is extended or adjusted under 35 U.S.C. 154(b) by 217 days.

(21) Appl. No.: 13/921,365

(22) Filed: Jun. 19, 2013

(65) Prior Publication Data

US 2014/0380530 A1    Dec. 25, 2014

(51) Int. Cl.
*A01H 5/10*    (2006.01)

(52) U.S. Cl.
CPC ........................................ *A01H 5/10* (2013.01)

(58) Field of Classification Search
None
See application file for complete search history.

(56) References Cited

U.S. PATENT DOCUMENTS 7,612,269 B2 * 11/2009 Jodari ........................ 800/320.2
8,841,525 B2 *  9/2014 Linscombe ................ 800/320.2

* cited by examiner

*Primary Examiner* — Medina A Ibrahim
(74) *Attorney, Agent, or Firm* — Sarfaraz Niazi

(57) ABSTRACT

A method for newly developed strain of rice that grows 6 feet tall with a record yield of 15 ton per hectare, 4 times the world average of 4 ton per hectare. The panicle is 47-50 cm long with 600-700 grains per panicle, with a stem diameter of 1.2 cm.

4 Claims, 1 Drawing Sheet

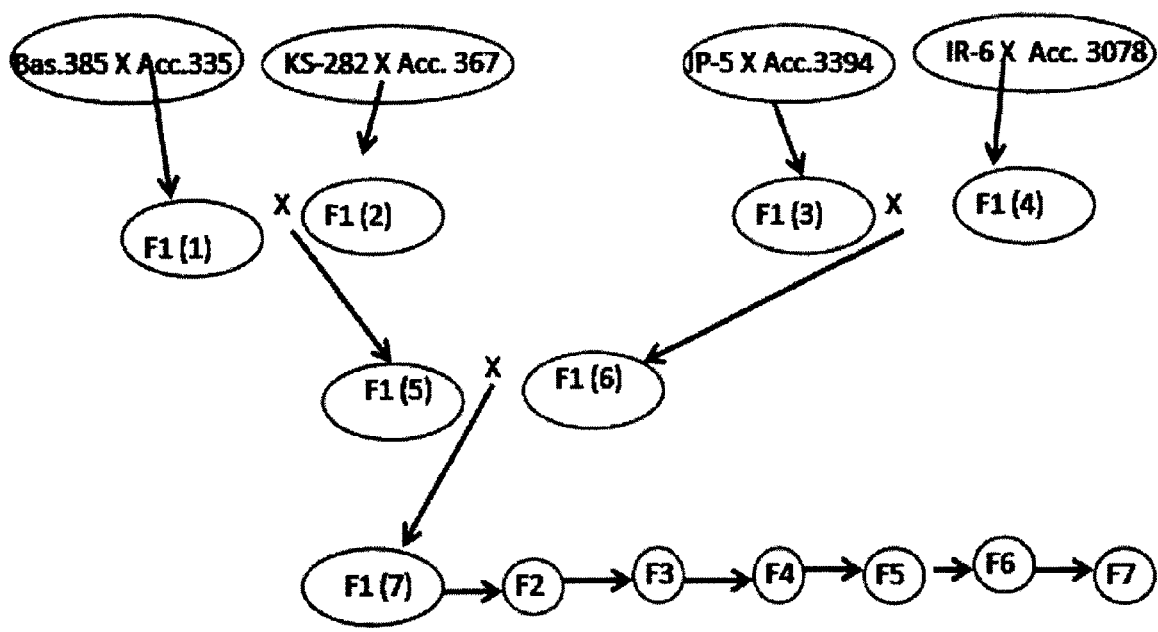
Diagrammatical representation of the development of Abbasi strain of rice

ABBASI STRAIN OF RICE

BACKGROUND OF THE INVENTION

Rice (*Oryza sativa* L.) is one of the most important food crops in the world, providing 35-60% of the dietary calories. It is consumed by more than 3 billion people. Rapid population growth and economic development are growing pressures for an increase in food production. To increase yield further and to break the yield ceiling, breeding efforts of scientists all over the world focused on expanding the yield sink capacity (the maximum size of sink organs to be harvested) mainly by increasing the number of spikelets per panicle (Kato et al 2007: Plant Production Science; 10: 442-450). As a result, cultivars with large panicles or extra-heavy panicle types with numerous spikelets per panicle have become available, such as the New Plant Type of the International Rice Research Institute and Super rice of China (Cheng et al., 2007 Annals of Botany 100, 959-966). These cultivars do not exhibited their high yield potential due to their poor grain-filling, as in a slow grain-filling rate and many unfilled grains (Ao et al., *Scientia Agricultura Sinica* 41, 1927-1936 (2008)), and World community was unable to increase potential yield of rice. The present invention is quite different from the approach of the other Rice Scientists of the World Community.

BRIEF SUMMARY OF THE INVENTION

The present invention provides a method to increase Source Capacity, increasing number of vascular bundles (food and water carrying organs), delaying Senescence (prolonging photosynthetic activities), increasing plant height with thick stem and increasing leaf area (enhancing the photosynthetic area of plant) along with increasing the Yield Sink capacity (the maximum size of sink organs to be harvested).

By using the above referred modification, panicle has been increased up to 45-50 cm, number of filled grains per panicle have been increased from 300 to 700 and potential yield has been increased from 5 ton to 15 ton per hectare.

BRIEF DESCRIPTION OF THE DRAWINGS

FIG. 1 is a diagrammatical representation of the development of the Abbasi strain of rice.

DETAILED DESCRIPTION OF THE INVENTION

The present invention involves eight parents comprising four commercial varieties of Pakistan viz. Basmati-385, JP-5, KS-282 and IR-6 and four land races from Pakistan viz. Acc. #335, Acc. #367, Acc. #3394 and Acc. #3078. These land races were selected on the basis of stem thickness, leaf area, panicle length, and potential yield. See Table 1 below.

TABLE 1

Characteristics of Land races used in the development of Abbasi Strain of Rice

| Characters | Accession # | | | |
|---|---|---|---|---|
| | 335 | 367 | 3394 | 3078 |
| Local name | 85-RGP-ARC | Mushkan | Byen | Sugdasi |
| Area of collection | Punjab Pakistan | Punjab pakistan | Chitral Pakistan | Sindh Pakistan |
| Productive tillers (no) | 19 | 16 | 18 | 14 |
| Plant height (cm) | 140 | 149 | 159 | 153 |
| Flag leaf area $Cm^2$ | 91 | 55 | 33 | 23 |
| Maturity (days) | 135 | 129 | 143 | 143 |
| Panicle length (cm) | 28 | 29 | 30 | 30 |
| Filled grain (no) | 226 | 114 | 116 | 83 |
| Harvest index | 0.32 | 0.30 | 0.30 | 0.38 |

The varieties were selected on the basis of their representation of the agro-ecological zones of whole Pakistan. The land races were crossed with Pakistani varieties and four F1 were produced as shown in FIG. 1.

The F1(1) was crossed with F1(2) to produce F1(5) and F1(3) was crossed with F1(4) to produce F1(6). The F1(5) was crossed with F1(6) to produce last F1(8). The last F1(7) was selfed to produce F2 population. The selection of the desired plants were started from F2 and continued until F7 progenies.

This approach differs from the IRRI New Plant Type Approach. IRRI used two parents for developing NPT and the present invention uses eight parents. The present invention uses land races of Pakistani origin comprising *Japonica* and *indica* rice however, IRRI used *Indica* and *Javanica* rice. IRRI focused on improvement of sink only (Food harvesting parts). The present invention focuses on improvement of both Sink (Food harvesting parts) and Source capacity (food manufacturing and transporting organs) like increasing plant height, leaf area, delaying senescence. IRRI used backcross method for the improvement of sink. The present invention does not use the backcross method Breaking the yield ceiling has been the challenge for rice scientist. Breeding efforts of scientists all over the world focused on increasing the number of spikelets per panicle. As a result, New Plant Type of the International Rice Research Institute and Super rice of China was developed. These cultivars do not exhibited their high yield potential due to their poor grain-filling and the World community was unable to break yield stagnation. The present invention is quite different from the approach of the other Rice Scientists of the World Community. The invention focuses on improvement of both sing size and source capacity that leads to development of a unique plant type with 15 ton per hectare potential yield.

TABLE 2

SPECIFICATION

| | |
|---|---|
| Genus | *Oryza* |
| Species | *sativa* |
| Habit of Growth | Growing with less water as well as in standing water |
| Plant Height | 6 ft |
| Panicle length | 40-50 cm |
| No of grains per panicle | 600-800 |
| Leaf length | 112 cm |

TABLE 2-continued

| | |
|---|---|
| Leaf width | 1.75-2 cm |
| No of nodes | 5 |
| Cultivar Name | Abbasi strain of rice |
| Vigor | Highly vigorous with stem diameter of 1.2 cm |
| Productivity | 100-170 g per plant or 15 Ton per hectare 4 times of world average |
| BOTANICAL CHARACTERISTICS | |
| Seedling color L. | Green |
| Days from seeding to flowering | 150 |
| Mature stem length (cm) | 165-190 cm |
| Stem attitude | Erect |
| Stem diameter | 1.2 cm |
| Stem stiffness | stiff |
| No. nodes/stem | 5 |
| Internode color | Green |
| Tillers/plant | 10-12 |
| Leaf length (cm) . . . | 112 |
| Length of leaf blade | 65 cm |
| Leaf width (cm) | 2 |
| Leaf color | Green |
| Leaf sheath color | Green |
| Leaf senescence | Late |
| Ligule color | |
| Light green | |
| Ligule length | 2-2.5 cm |
| Ligule shape | 2-cleft |
| Collar color | Pale green |
| Flag leaf attitude | Erect |
| Panicle length | 36-50 cm |
| Panicle type | Compact |
| Panicle exsertion | Well exserted |
| Awning at flowering | Absent |
| Awning at Maturity | Short & partly |
| Sterility | V. low |
| Shattering | Moderate High |
| Thresh ability | Easy |
| SEED CHARACTERISTICS | |
| Stigma color | White |
| Apiculus color (anthesis) | Purple green |
| Husk color | Straw |

TABLE 2-continued

| | |
|---|---|
| Husk pigmentation | Absent |
| Husk pubescence | Absent |
| Seed length (mm) | 10 |
| Seed width (mm) | 2 |
| Seed thickness (mm) | 1 |
| Seed size | Extra long |
| 000, seed weight (g) | 40 |
| Yield (kg/ha) | 15 T/ha |
| KERNAL CHARACTERISTICS | |
| Kernal size | Long |
| Kernal length/bradth ratio | 3.5 |
| Kernal color | Off white |
| Kernal appearance | Translucent |
| Kernal chalkiness | Absent |
| Kernal quality | Medium fine |
| Kernal aroma | Weak |
| Fertility | Highly Fertile, panicle have 600-720 fertile grains |

What is claimed is:

1. A plant of the Abbasi strain of rice, seed of said Abbasi strain of rice has been deposited in NARC accession no. 32940, wherein said rice plant is produced from first crossing Bas 385 and ACC335 to give F1(1), KS-282 and ACC367 to give F1(2), JP-5 and ACC3394 to give F1(3), IR-6 and ACC3078 to give F1(4), then crossing F1(1) and F1(2) to give F1(5), crossing F1(3) and F1(4) to give F1(6) and finally crossing F1(5) with F1(6) to give F1(7).

2. The Abbasi strain of rice plant according to claim 1, which has a mature height of about 120 cm to about 140 cm; and, produces rice grains having an average length of about 8 mm to about 10 mm, an average width of about 1.8 to 2.2 mm to about 1.9 mm, and an average thickness of about 0.8 to 1.2 mm.

3. The Abbasi strain of rice plant of claim 1, wherein said plant produces about 14 to 16 tons per hectare.

4. The Abbasi strain of rice of claim 1 wherein F1(7) is then selfed to produce segregating population from F2 to F7.

* * * * *